United States Patent
Ait-Oufella

(10) Patent No.: US 10,556,953 B2
(45) Date of Patent: Feb. 11, 2020

(54) AGENT CAPABLE OF DEPLETING CD8 T CELLS FOR THE TREATMENT OF MYOCARDIAL INFARCTION OR ACUTE MYOCARDIAL INFARCTION

(71) Applicants: INSERM (Institut National de Sante et de la Recherche Medicale), Paris (FR); Universite Paris Descartes, Paris (FR); Assitance Publique-Hopitaux de Paris (APHP), Paris (FR)

(72) Inventor: Hafid Ait-Oufella, Paris (FR)

(73) Assignees: INSERM (Institut National de la Santé et de la Recherche Médicale), Paris (FR); Université Paris Descartes, Paris (FR); Assistance Publique-Hôpitaux de Paris (APHP), Paris (FR)

( * ) Notice: Subject to any disclaimer, the term of this patent is extended or adjusted under 35 U.S.C. 154(b) by 133 days.

(21) Appl. No.: 15/759,850

(22) PCT Filed: Oct. 11, 2016

(86) PCT No.: PCT/EP2016/074292
§ 371 (c)(1),
(2) Date: Mar. 14, 2018

(87) PCT Pub. No.: WO2017/064034
PCT Pub. Date: Apr. 20, 2017

(65) Prior Publication Data
US 2018/0251552 A1    Sep. 6, 2018

(30) Foreign Application Priority Data
Oct. 12, 2015  (EP) ..................... 5306612

(51) Int. Cl.
*C07K 16/28* (2006.01)
*A61K 47/68* (2017.01)
*A61K 39/00* (2006.01)

(52) U.S. Cl.
CPC ...... *C07K 16/2815* (2013.01); *A61K 47/6849* (2017.08); *A61K 2039/505* (2013.01)

(58) Field of Classification Search
None
See application file for complete search history.

(56) References Cited

U.S. PATENT DOCUMENTS

| | | | |
|---|---|---|---|
| 6,673,604 B1* | 1/2004 | Edge | C12N 5/0656 424/93.21 |
| 2011/0150879 A1* | 6/2011 | Rabb | C07K 16/2803 424/137.1 |
| 2015/0010581 A1* | 1/2015 | Lewis | A61K 39/39541 424/173.1 |

OTHER PUBLICATIONS

Skorska et al., J Cell Mol Med. Aug. 2015;19(8):1975-85. (Year: 2015).*
EMedicine, "Myocardial Infarction," pp. 1-72, May 7, 2019. (Year: 2019).*
Knowlton (J Mol Cell Cardiol 32, 2107-2110 (2000)). (Year: 2000).*
Curato et al. (J Immunol. Nov. 15, 2010;185(10):6286-93). (Year: 2010).*
Varda-Bloom et al.; "Cytotoxic T lymphocytes are activated following myocardial infarction and can recognize and kill healthy myocytes in vitro"; Journal of Molecular and Cellular Cardiology, vol. 32, No. 12, Dec. 1, 2000, pp. 2141-2149.
Maisel et al.; "Experimental Autoimmune Myocarditis Produced by Adoptive Transfer of Splenocytes After Myocardial Infarction"; Circulation Research, vol. 82, No. 4, Mar. 9, 1998, pp. 458-463.
Yan et al.; "Temporal dynamics of cardiac immune cell accumulation following acute myocardial infarction"; Journal of Molecular and Cellular Cardiology, vol. 62, Sep. 1, 2013, pp. 24-35.
Mracsko et al.; "Antigen Dependently Activated Cluster of Differentiation 8-Positive T Cells Cause Perforin-Mediated Neurotoxicity in Experimental Stroke"; Journal of Neuroscience, vol. 34, No. 50, Dec. 10, 2014, pp. 16784-16795.

* cited by examiner

*Primary Examiner* — Zachary S Skelding
(74) *Attorney, Agent, or Firm* — W & C IP

(57) ABSTRACT

The present invention relates to a method for treating MI or AMI in a subject in need thereof comprising a step of administering to said subject a therapeutically effective amount of an agent capable of depleting CD8 T cells. More particularly, this present invention relates to a method for treating acute myocardial infarction by reducing the size of necrosis and limiting 10 the post ischemic left ventricular remodeling.

3 Claims, 14 Drawing Sheets
Specification includes a Sequence Listing.

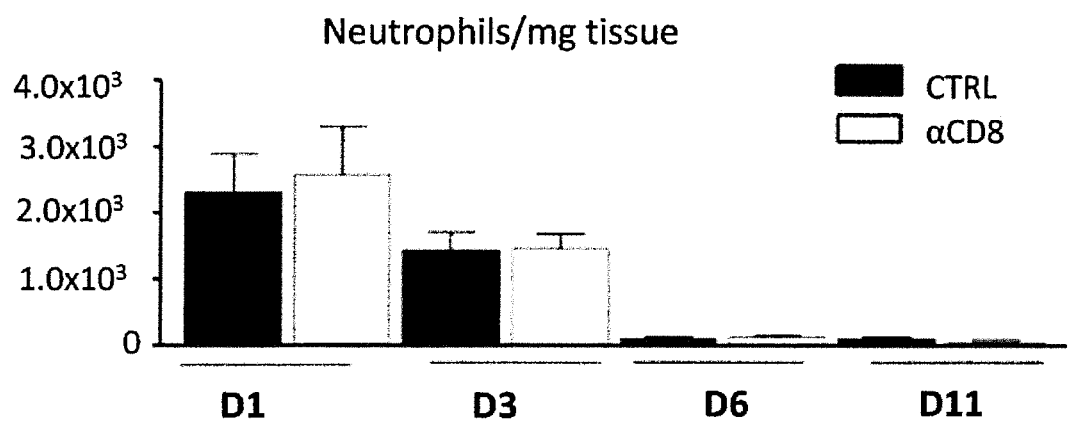
Figure 3 (1/4)
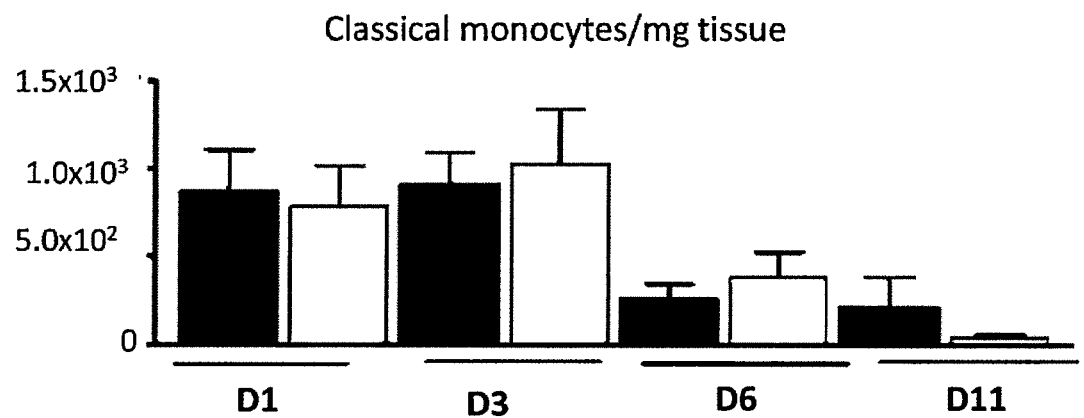
Figure 3 (2/4)
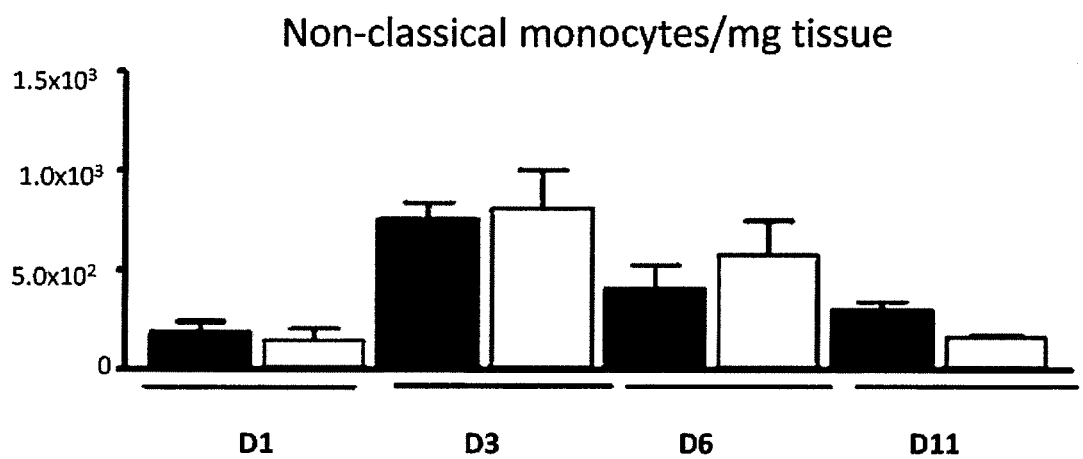
Figure 3 (3/4)

Figure 4B:
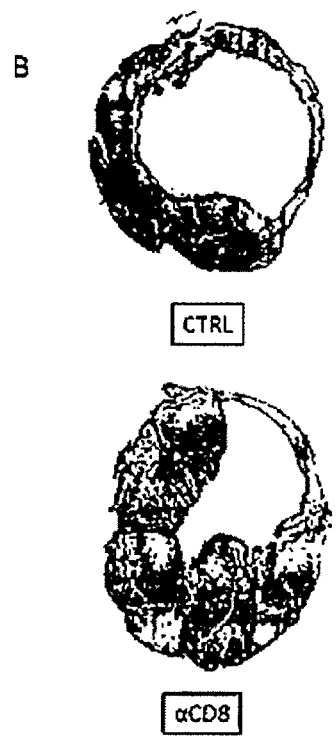

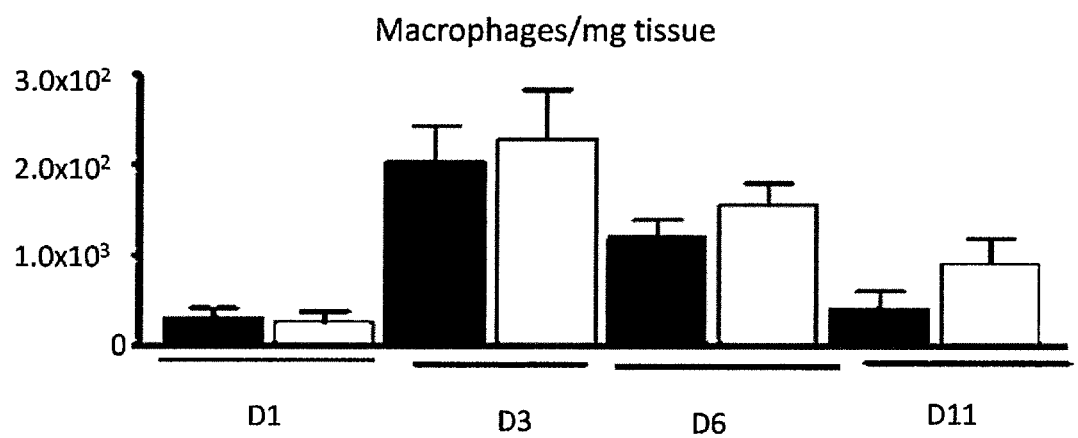
Figure 3 (4/4)
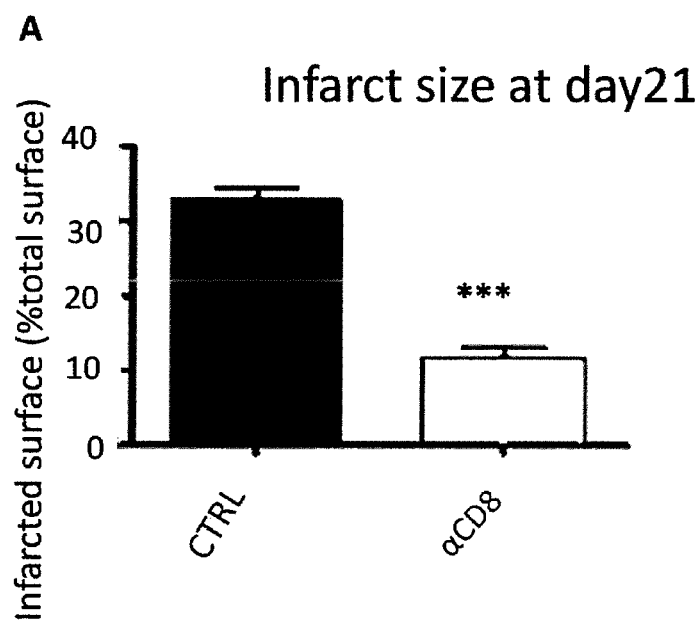
Figure 4A

Figure 5A:
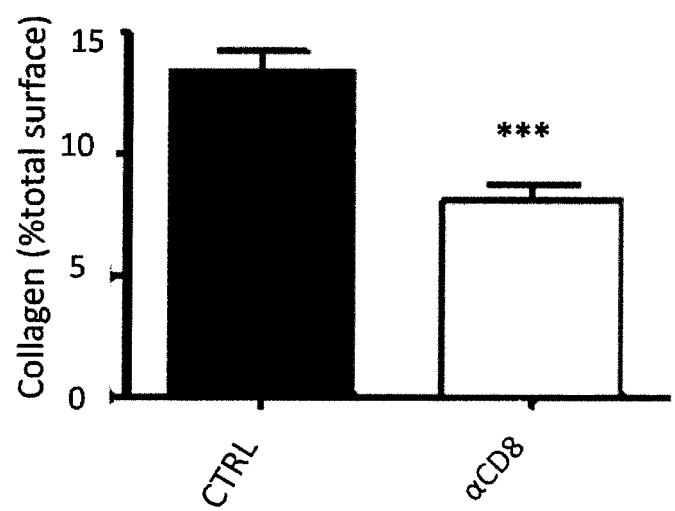

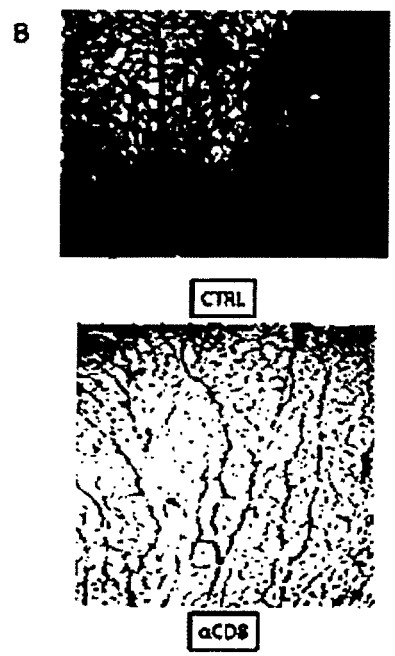
Figure 5B
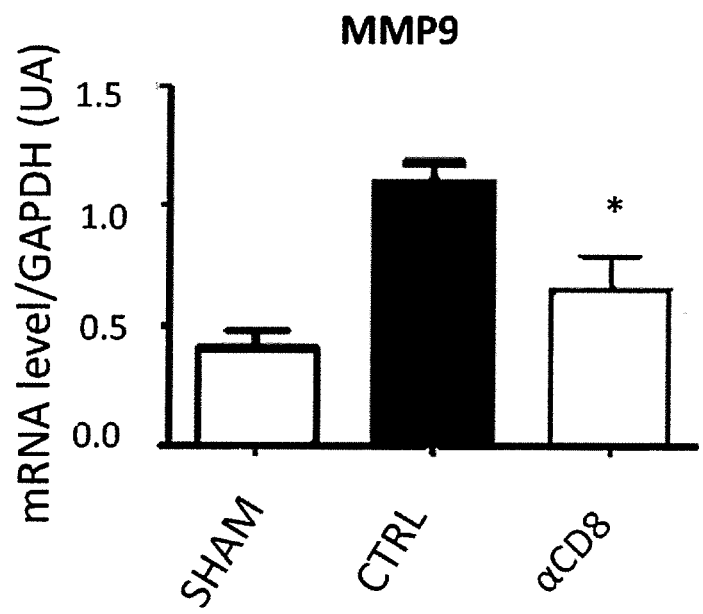
Figure 6 (1/3)

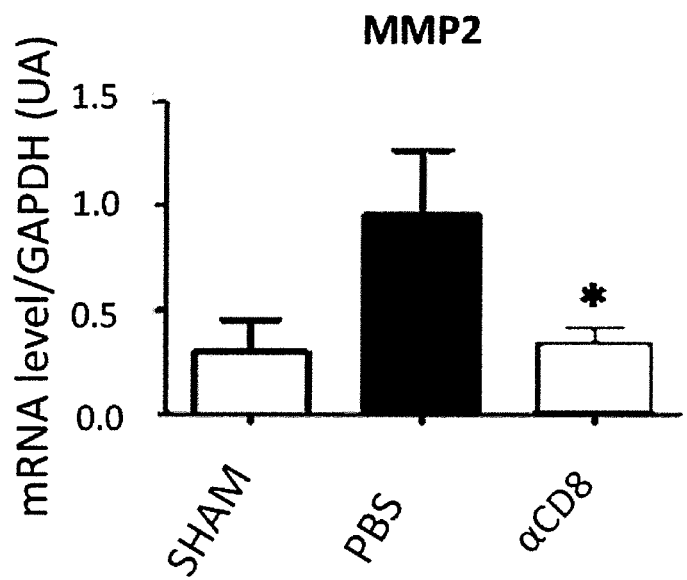
Figure 6 (2/3)
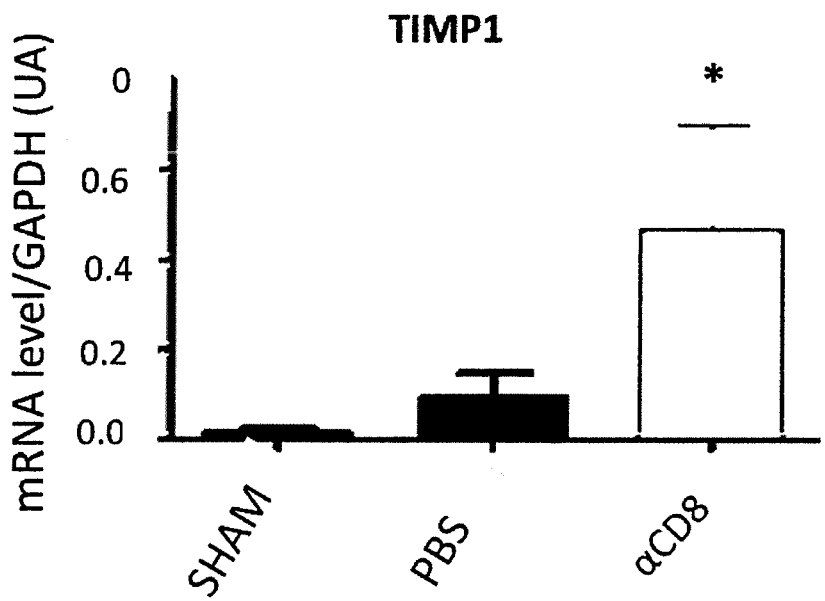
Figure 6 (3/3)

D

E

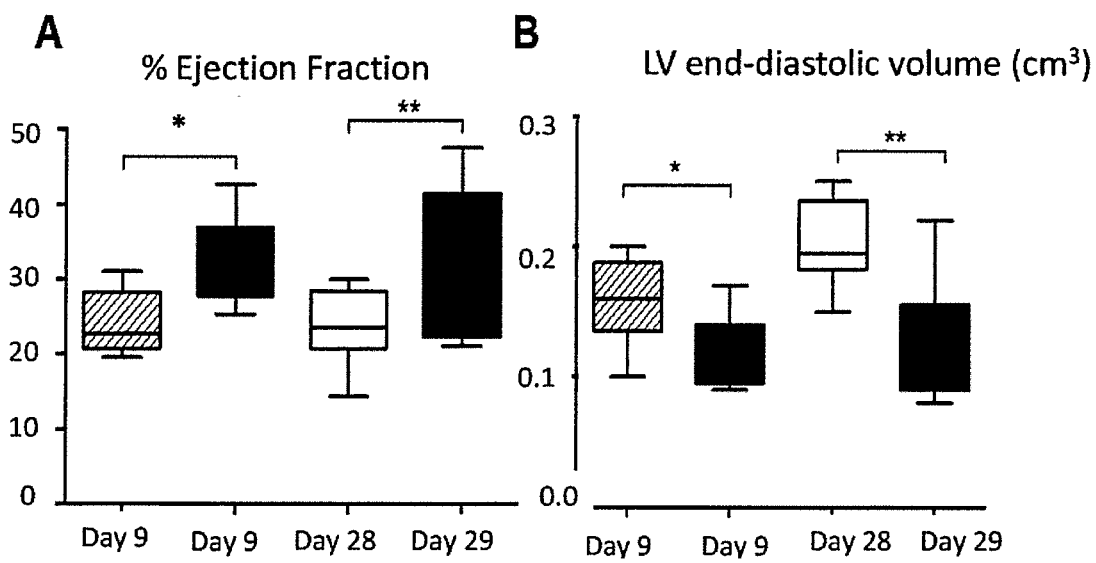
Figure 10 A-B
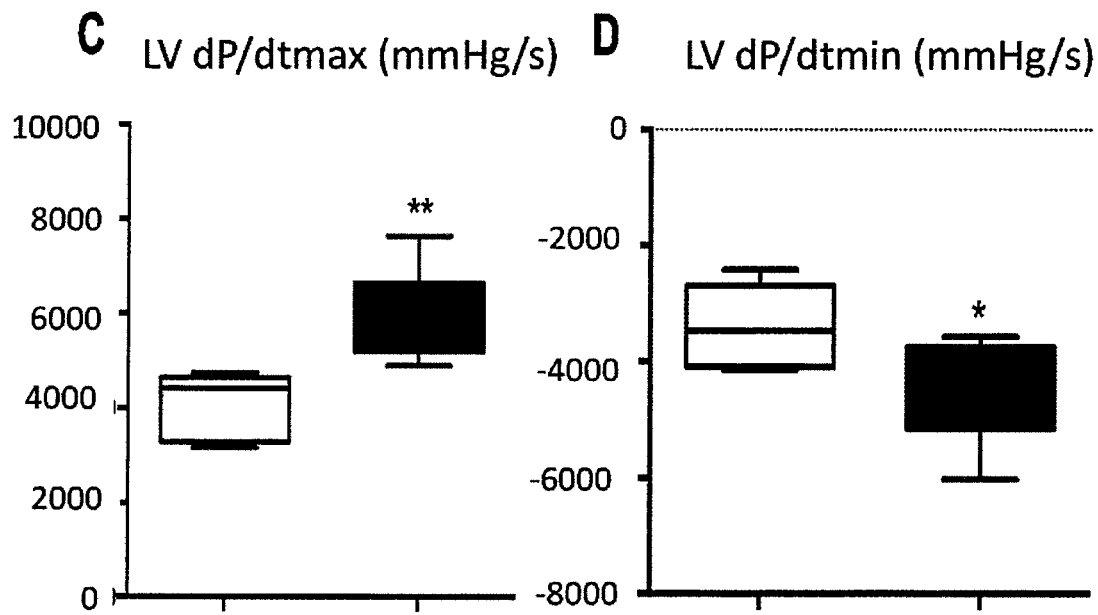
Figure 10 C-D

AGENT CAPABLE OF DEPLETING CD8 T CELLS FOR THE TREATMENT OF MYOCARDIAL INFARCTION OR ACUTE MYOCARDIAL INFARCTION

FIELD OF THE INVENTION

The present invention relates to an agent capable of depleting CD8 T cells for the treatment of myocardial infarction or acute myocardial infarction.

BACKGROUND OF THE INVENTION

Myocardial Infarction (MI) or Acute Myocardial Infarction (AMI) is defined as necrosis of cardiomyocytes due to the temporary or permanent ischemia in the areas of one or more coronary arteries. The MI or AMI is the leading cause of death in industrialized countries, in France with 120,000 cases reported in 2014, including 18 000 deaths. The generalization of coronary angioplasty, fibrinolytic and antithrombotic treatments resulted in a significant decline in mortality at one month, around 5% in large randomized trials [1]. But these encouraging results should not obscure the growing incidence of post-infarction heart failure. Indeed, the MI or AMI can result in a deleterious remodeling involving left ventricular dilation decreased heart contractile function exposure to the risk of heart failure.

It is currently accepted that part of myocardial damage during coronary occlusion are not directly related to tissue hypoxia. Transient or permanent myocardial ischemia induces the recruitment of inflammatory cells of the innate and adaptive immunity in the myocardium [2]. Several studies have shown that neutrophils and monocytes involved in conventional deleterious remodeling by producing pro-inflammatory cytokines, oxygen free radicals and matrix proteases. [3] There are over thirty years, Romson et al. had already reported the pathogenic role of neutrophils in an infarction model in dogs showing a decrease in the size of the infarct in the depletion of neutrophils [4].

The role of lymphocytes has been explored only recently. In their laboratory, inventors have shown that mature B2 lymphocytes play a deleterious role in postischemic ventricular remodeling in particular producing a CCL-7 chemokine that promotes the recruitment of monocytes from the bone marrow into the blood and then to the myocardium ischemic [5]. The overall role of CD4 T cells remains controversial. It has been shown that T lymphocyte subpopulation called regulatory CD4+Foxp3+protects against postischemic remodeling through the production of anti-inflammatory mediators such as IL-10 and TGF-β [6]. Similarly, the role of CD8 T cells remains also controversial. The role of cytotoxic CD8 T cells has never been studied in vivo. One study reported that the in vitro CD8 T cells may induce apoptosis in rat cardiomyocytes [7] but a recent study (Curato et al 2010) suggests that a subtype of CD8 T cells is increased after acute MI and has a cardioprotective role during MI. Thus, there is a need to understand clearly the role of CD8 T cells during MI.

SUMMARY OF THE INVENTION

The present invention relates to an agent capable of depleting CD8 T cells for the treatment of myocardial infarction or acute myocardial infarction. In particular, the present invention is defined by the claims.

DETAILED DESCRIPTION OF THE INVENTION

For the first time, the inventors have shown that the CD8 T cells depletion by injection of an anti-CD8 monoclonal antibody in a mouse model of myocardial infarction induced a significant reduction in the size of necrosis, reduced deleterious remodeling such as evidenced by the decrease in fibrosis peri-necrotic and causes a deviation of the local immune response to an anti-inflammatory profile. These results could provide a new therapeutic approach to limit deleterious left ventricular remodeling in post-myocardial infarction.

These results suggest that depletion of CD8 T cells is beneficial for the treatment of MI or AMI.

Method of Treatment

The present invention relates to a method for treating MI or AMI in a subject in need thereof comprising a step of administering to said subject a therapeutically effective amount of an agent capable of depleting CD8 T cells. More particularly, this present invention relates to a method for treating acute myocardial infarction by reducing the size of necrosis and limiting the post ischemic left ventricular remodeling.

In some embodiments, the agent capable of depleting CD8 T cells is an antibody. In a particular embodiment, the antibody as used herein is a monoclonal antibody.

In some embodiments, according to this invention, the method of treatment is suitable to reduce necrosis size post infarction.

In some embodiments, according to this invention, the method of treatment is suitable to reduce infracted zone.

In some embodiments, according to this invention, the method of treatment is suitable to reduce side effects of remodeling.

As used, herein, the term "CD8 T cells" refers to T cells expressing T-cell receptors (TCRs) that can recognize a specific antigen. More particularly, the term"CD8 T cells", refers to T cells which carry the co-receptor CD8. CD8 is a transmembrane glycoprotein that serves as a co-receptor for the TCR. Like the TCR, CD8 binds to a major histocompatibility complex I (MHC I) molecule. "CD8 T cells" differentiate into cytotoxic CD8 T cells, and kill cancer cells and cells infected particularly by viruses by two ways. First way consist of releasing cytotoxins such as perforin and granzymes. The second way consist of inducing apoptosis by cell-surface interaction between the CD8 T cells and the infected cell (FAS-L which is present on CD8 T cells and FAS which is present on the target cell). Thus, CD8 T cells are called cytotoxic T lymphocytes (CTL), T-killer cell, cytolytic T cells, CD8+ T cells or killer T cells.

As used herein, the term "agent capable of depleting CD8 T cells" refers to a molecule which depletes or destroys CD8 T cells in a patient and/or interferes with one or more CD8 T cells functions, e.g. by reducing or preventing cytotoxic activity elicited by CD8 T cells. Typically, the agent capable of depleting CD8 T cells binds to a CD8 T cells surface marker. Typically, the agent capable of depleting CD8 T cells is able to deplete CD8 T cells (i.e. reduce circulating CD8 T cells levels) in a patient treated therewith. Such depletion may be achieved via various mechanisms such as antibody-dependent cell mediated cytotoxicity (ADCC) and/or complement dependent cytotoxicity (CDC), inhibition of CD8 T cells proliferation and/or induction of CD8 T cells death (e.g. via apoptosis). Agents capable of depleting CD8 T cells include but are not limited to antibodies, synthetic or native sequence peptides and small molecule antagonists which bind to the CD8 T cells, optionally conjugated with or fused to a cytotoxic agent. Typically the agent depleting CD8 T cells is an antibody.

As used herein, the term "antibody" is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

In some embodiments, the antibody is a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Typically, "chimeric antibody" refers to an antibody which comprises a VH domain and a VL domain of a murine antibody, and a CH domain and a CL domain of a human antibody. Chimeric antibodies include PRIMATTZED® antibodies wherein the antigen-binding region of the antibody is derived from an antibody produced by, e.g., immunizing macaque monkeys with the antigen of interest.

In some embodiments, the antibody is a humanized antibody. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR (Hyper Variable Regions) of the recipient are replaced by residues from a HVR of a non-human species (donor antibody) such as mouse, rat, rabbit, or nonhuman primate having the desired specificity, affinity, and/or capacity. In some instances, FR (Framework Regions) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087, 409.

In some embodiments, the antibody is a human antibody. A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad.

Sci. USA, 103:3557-3562 (2006) regarding human antibodies generated via a human B-cell hybridoma technology.

In some embodiments, the antibody is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb. For a general description of single domain antibodies, reference is made to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, agent capable of depleting CD8 T cells is a monoclonal antibody. Monoclonal antibodies can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique.

In some embodiments, the antibody is an anti-CD8 T cells monoclonal antibody-drug conjugated (ADC). An "anti-CD8 T cells monoclonal antibody-drug conjugate" as used herein refers to an anti-CD8 T cells monoclonal antibody according to the invention conjugated to a therapeutic agent. In typical embodiments, an anti-CD8 T cells monoclonal antibody is conjugated to a cytotoxic agent. Any cytotoxic agent well known by the skilled person may be used. ADC may be immunoconjugtes or bioconjugates. Typically immunoconjugates ADC are antibodies conjugated to a second molecule which is a cytotoxic agent or a growth inhibitory agent. The term "cytotoxic agent" as used herein refers to a substance that inhibits or prevents the function of cells and/or causes destruction of cells. A "growth inhibitory agent" when used herein refers to a compound or composition which inhibits growth of a cell, especially CD8 T cells, either in vitro or in vivo. Typically, cytotoxic agent or a growth inhibitory agent may be a toxin, radioisotope or label. Examples of growth inhibitory agents include agents that block cell cycle progression, such as agents that induce G1 arrest and M-phase arrest. Typically, monoclonal antibodies of this invention are conjugated to a cytotoxic agent via a linker. Antibodies of this invention track these proteins down in the body and attach themselves to the surface of CD8 T cells. The biochemical reaction between the antibody and the target protein triggers a signal in the CD8 T cells, which then absorbs or internalizes the antibody together with the cytotoxic agent. After the ADC is internalized, the cytotoxic drug is released and kills the CD8 T cells. Typically, bioconjugates ADC are antibodies produced by a chemical strategy to form a stable covalent link between two molecules with at least one of which is a biomolecule. In some embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, CD8 T cell depleting agent is a fusion protein.

Conjugation of the antibodies of the invention with cytotoxic agents or growth inhibitory agents may be made using a variety of bi-functional protein coupling agents. Alternatively, a fusion protein comprising the monoclonal antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

In some embodiments, the anti-CD8 T cells monoclonal antibody of the invention is used to induce antibody dependent cellular cytotoxicity (ADCC). ADCC refers to a form of cytotoxicity in which antibodies bound onto Fc receptors (FcRs) present on certain cytotoxic cells (e.g. Natural Killer cells, NK cells). These cytotoxic effector cells are able to bind specifically to an antigen-bearing target cell and subsequently kill the target cell. ADCC involves in activation of NK cells by antibodies of the present invention. NK cells express CD16 which is an Fc receptor. This receptor recognizes, and binds to, the Fc portion of antibodies of the present invention which has bound to the surface of CD8 T cells. The most common Fc receptor on the surface of an NK cell is called CD16 or FcγRIII. Typically, in the context of the present invention, an anti-CD8 T cells monoclonal antibody comprising an Fc region with effector function is used to induce antibody dependent cellular cytotoxicity. Methods for inducing ADCC generally include contacting the CD8 T cells with an effective amount an anti-CD8 T cells monoclonal antibody comprising an Fc region having ADCC activity, wherein the contacting step is in the presence of a cytolytic immune effector cell expressing an Fc receptor having cytolytic activity. Immune effector cells expressing cytolytic Fc receptors (e.g., FcγRIIIα or CD16) include, for example, NK cells. Once the Fc receptor binds to the Fc region of the anti-CD8 T cells monoclonal antibody of the present invention, the NK cell releases cytokines (such as IFN-γ) and granzymes/perforines which kill CD8 T cells.

In some embodiments, the anti-CD8 T cells monoclonal antibody of the invention is used to induce a complement dependent cytotoxicity (CDC). CDC refers to the lysis of a target cell in the presence of complement. Activation of the classical complement pathway is initiated by the binding of the first component of the complement system to antibodies of the present invention, which are bound to CD8 T cells. CDC is initiated when C1q, the initiating component of the classical complement pathway is fixed to the Fc portion of target-bound antibodies. Briefly, the antibodies of the present invention are directed against CD8 T cells, the portion Fc of antibodies are recognised by C1q of the classical complement pathway and triggers a cascade which induces lysis of CD8 T cells.

In some embodiments, the anti-CD8 T cells monoclonal antibody of the invention interfere in CD8 T cells signalling pathway. Typically, the anti-CD8 T cells monoclonal antibody of the present invention interact with CD 8, the surface marker and inhibits CD8 interaction with co-stimulation molecules which are needed to the activation of CD8 T cells.

In some embodiments, the anti-CD8 T cells monoclonal antibody induces CD8 T cells death. (e.g. via apoptosis).

In some embodiments, the anti-CD8 T cells antibody is monospecific, bispecific, trispecific, or of greater multispecificity. Multispecific antibodies, including bispecific and trispecific antibodies, useful for practicing the methods described herein are antibodies that immunospecifically bind to both CD8 T cells and a second cell surface receptor or receptor complex that mediates ADCC, phagocytosis, and/or CDC, such as CD16/FcgRIII, CD64/FcgRI, killer inhibitory or activating receptors, or the complement control protein CD59. In a typical embodiment, the binding of the portion of the multispecific antibody to the second cell surface molecule or receptor complex enhances the effector functions of the anti-CD8 T cells antibody. In some embodiments, the anti-CD8 T cells antibody is a bispecific antibody. The term "bispecific antibody" has its general meaning in the art and refers to any molecule consisting of one binding site for a target antigen on CD8 T cells and a second binding side for an activating trigger molecule on an effector cell, such as CD16 (FcγRIII) on natural killer (NK) cells, monocytes and macrophages, CD89 (FcαRI) and CD64 (FcγRI) on neutrophils and monocytes/macrophages, and DEC-205 on dendritic cells. According to the invention, the bispecific antibody comprises a binding site for CD8 T cells. A part from the specific recruitment of the preferred effector cell population, bispecific antibodies avoid competition with endogenous immunoglobulin G (IgG) when the selected binding site for the trigger molecule on the effector cell does not overlap with Fc-binding epitopes. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, EMBO J. 10:3655-59. In the context of the invention, the term "treatment" or "treat" as used herein, refers to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

A "therapeutically effective amount" is intended for a minimal amount of active agent which is necessary to impart therapeutic benefit to a subject. For example, a "therapeutically effective amount" to a patient is such an amount which induces, ameliorates or otherwise causes an improvement in the pathological symptoms, disease progression or physiological conditions associated with or resistance to succumbing to a disorder.

The term "subject" refers to any mammals, such as a rodent, a feline, a canine, and a primate. Particularly, in the present invention, the subject is a human afflicted with or susceptible to be afflicted with MI or AMI.

Pharmaceutical Composition

In a particular embodiment, the present invention relates to a pharmaceutical composition comprising an agent capable of depleting CD8 T cells. The agent capable of depleting CD8 T cells of the invention may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The agent capable of depleting CD8 T cells of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The agent capable of depleting CD8 T cells according to this invention, may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

Figure 1:
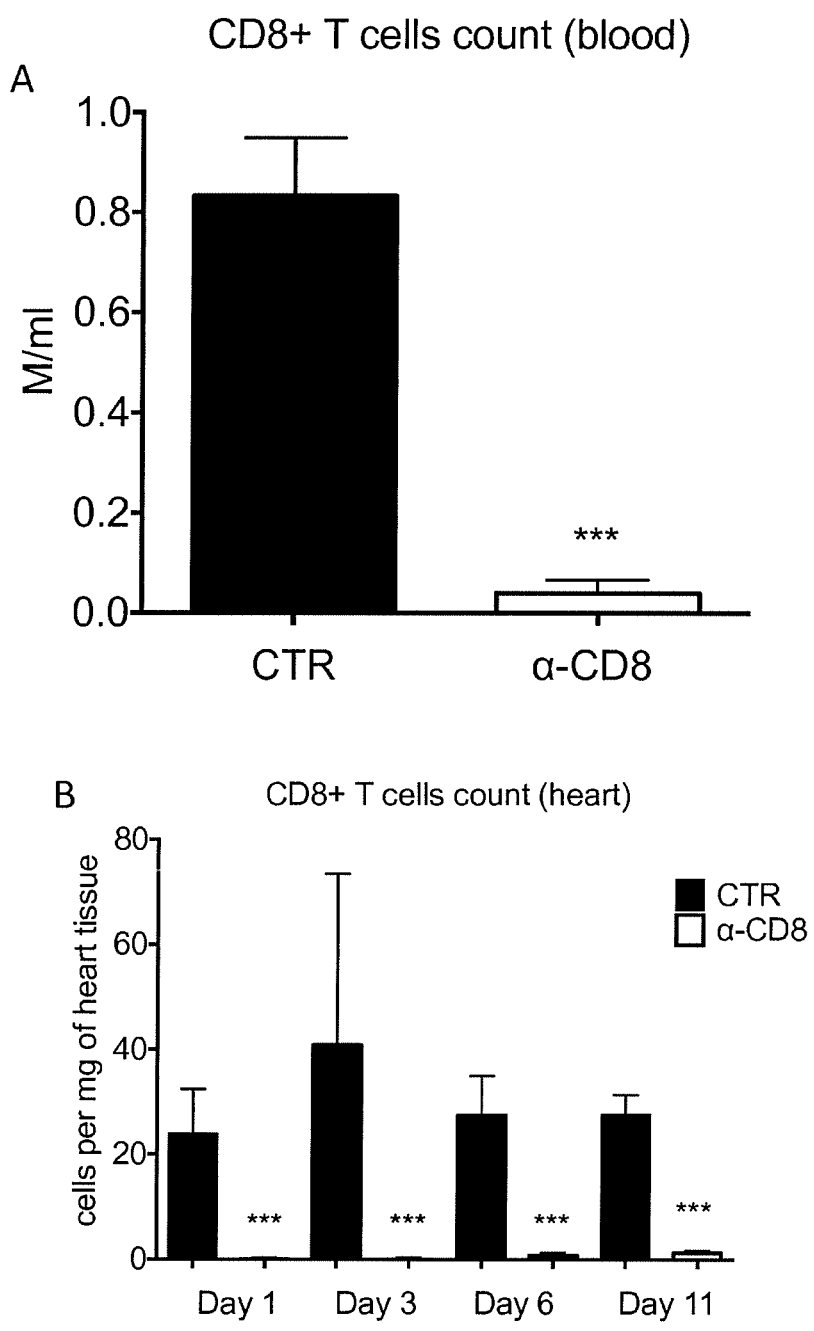

FIG. 1: CD8 T cell depletion in the blood at day 3 (A). Kinetic of the depletion in the myocardium, coronary ligation was done at day 0. $P<0.0001$. (n=6-8/group) (B)

Figure 2:
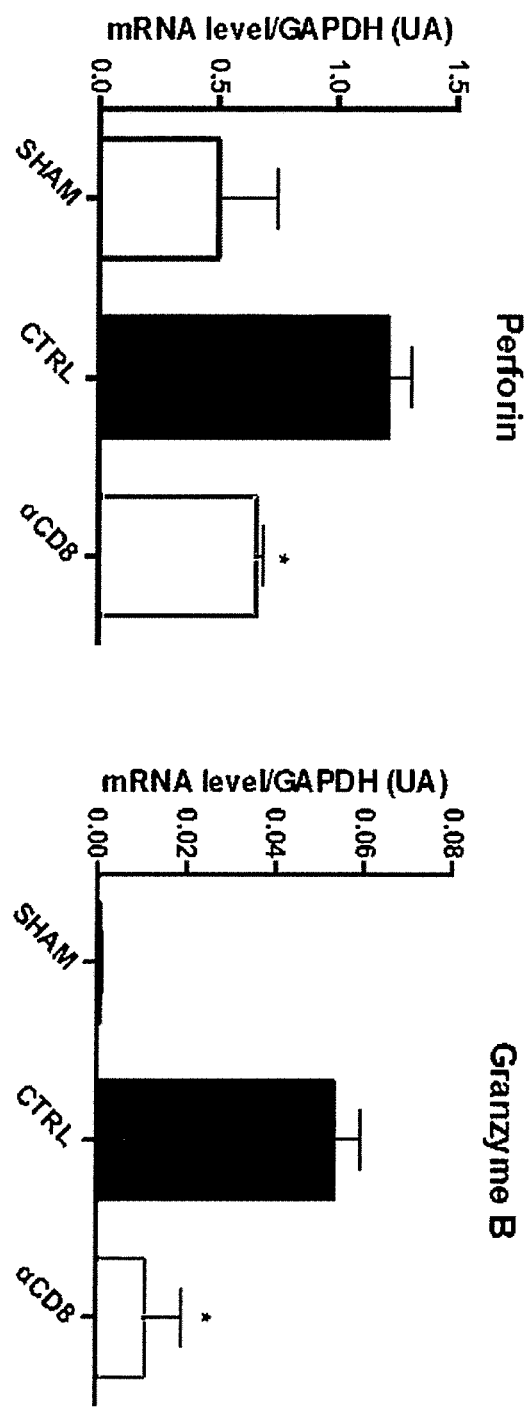

FIG. 2: Perforin and Granzyme B mRNA quantification at day 7 after MI by qPCR in the ischemic heart, *$P<0.05$. (n=6-8/group).

FIG. 3: Kinetics of infiltration of immune cells within the ischemic myocardium: Quantitative analysis of the cellular infiltration by flow cytometry. (n=6-8/group/time point).

FIG. 4: infarct size at D21: Quantitative analysis (A) and representative pictures (B) of infarcted area within the myocardium. In red/purple and blue healthy myocardium and green the infarcted area ***$P<0.001$. (n=12/group).

FIG. 5: Interstitial fibrosis at Day 21 in the peri-infarct area. Quantitative Analysis (A) and representative pictures (B) of interstitial fibrosis stained with Sirius Red. Yellow for cardiomyocytes and Red for collagen fibers and reticulin, ***: $P<0.005$. (n=12/group).

FIG. 6: Gene expression by qPCR, 7 days after coronary ligation. (n=4-6/group).

Figure 7A:
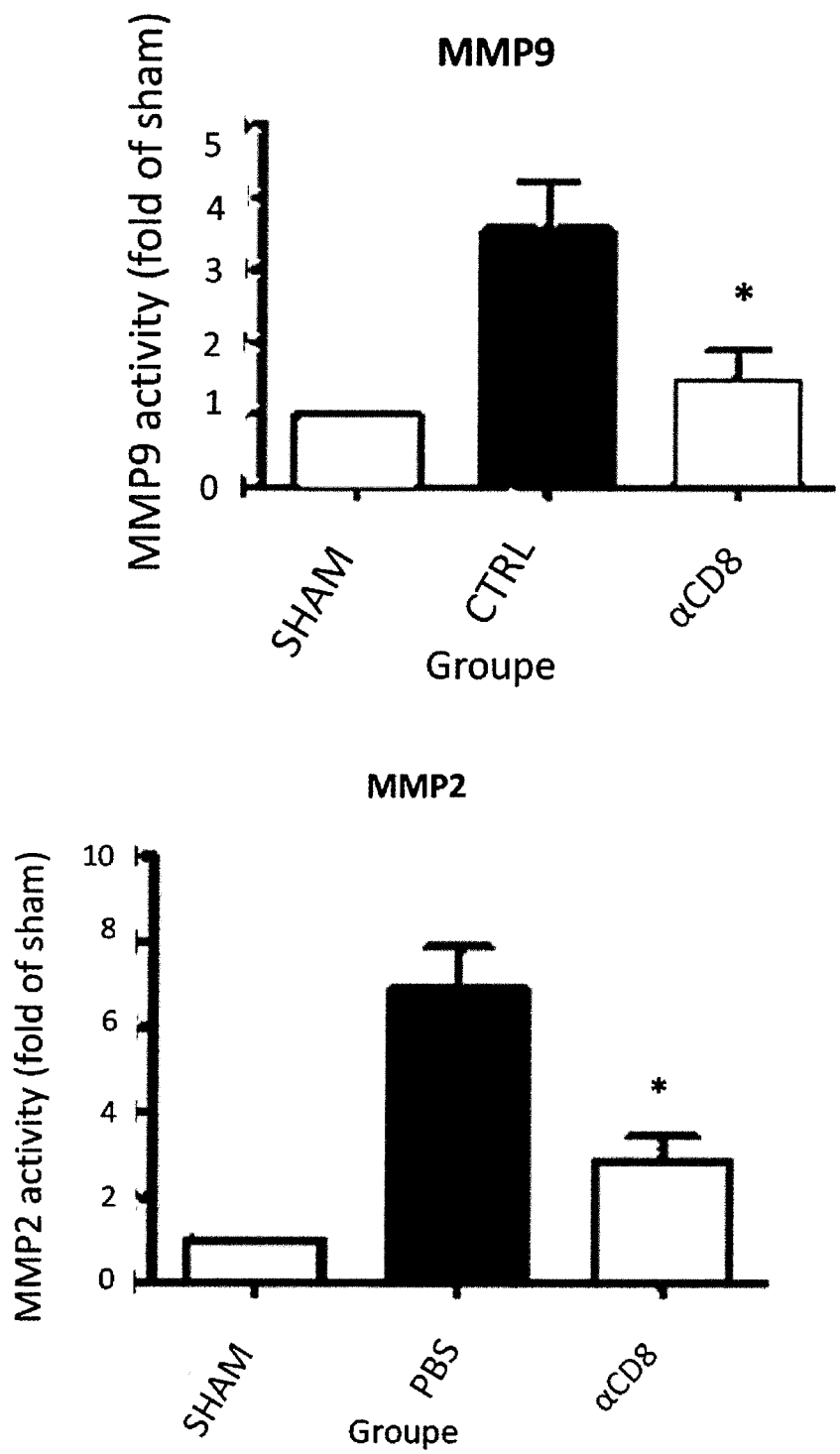
Figure 7B:
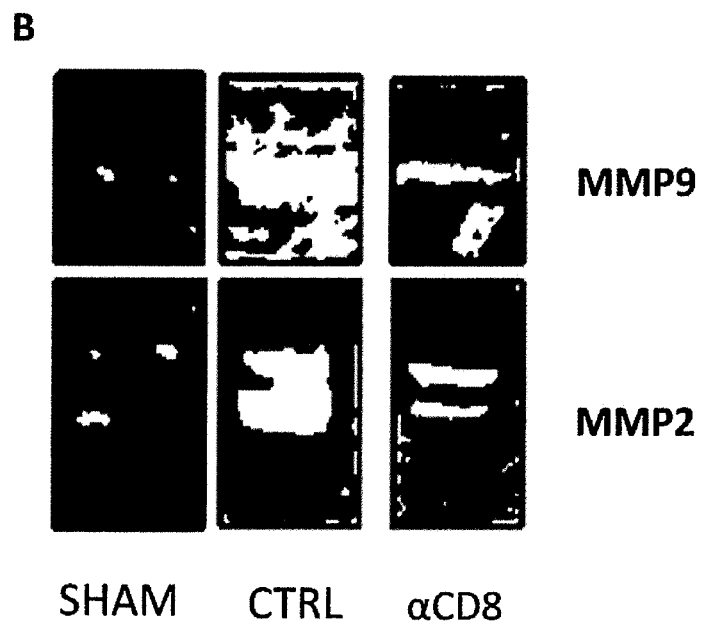
Figure 8A:
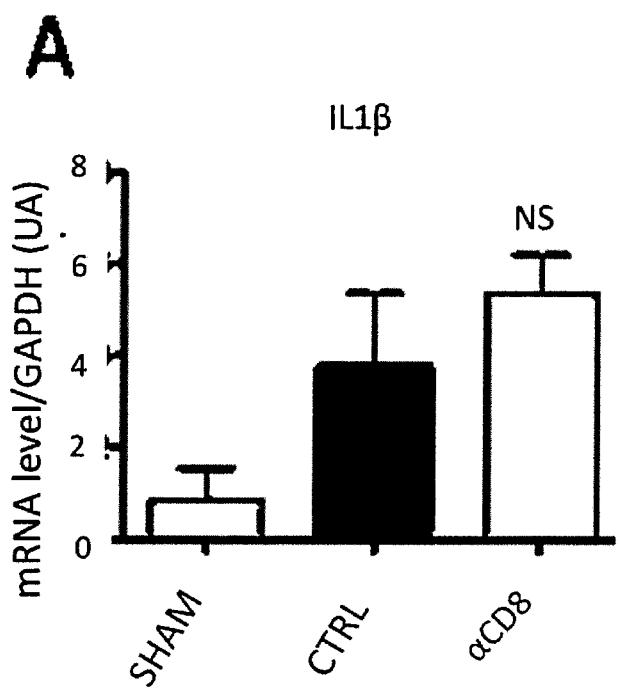
Figure 8B:
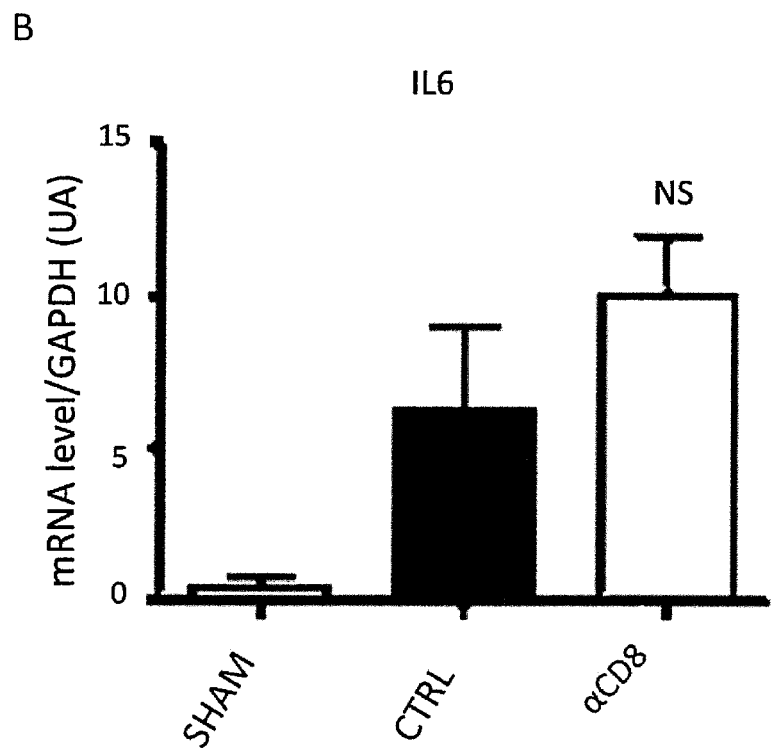
Figure 8C:
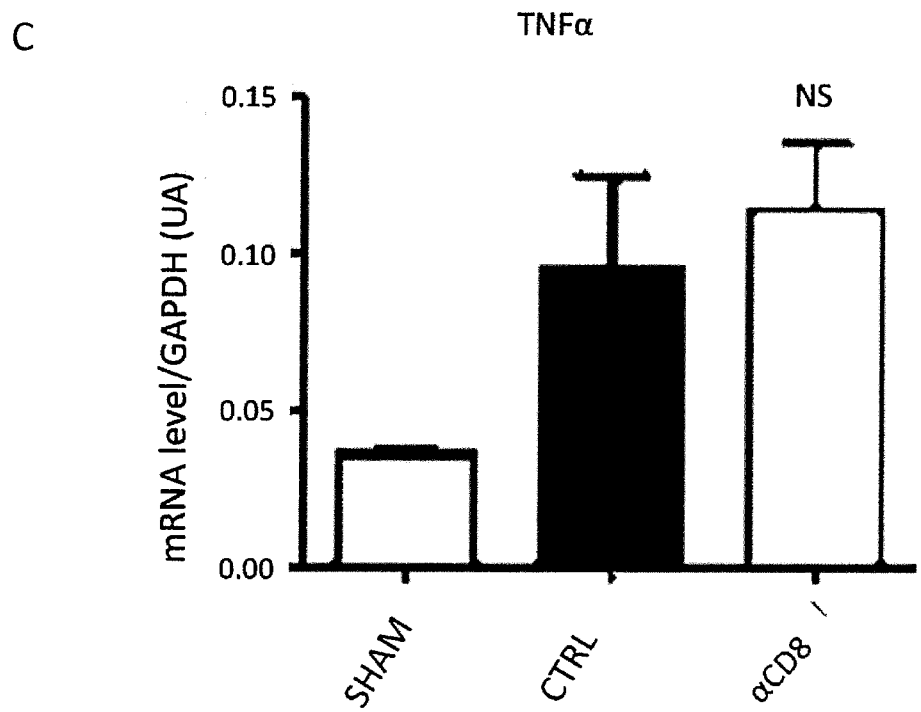
Figure 8D:
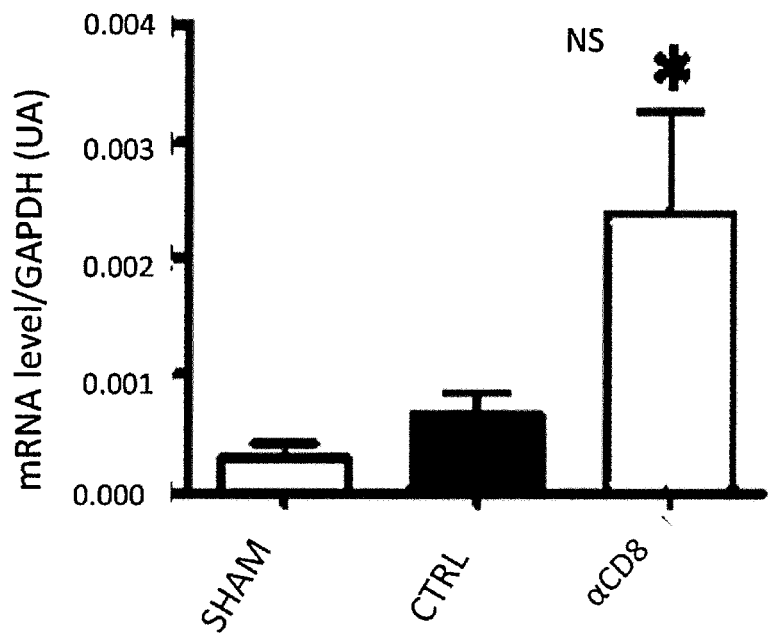
Figure 8E:
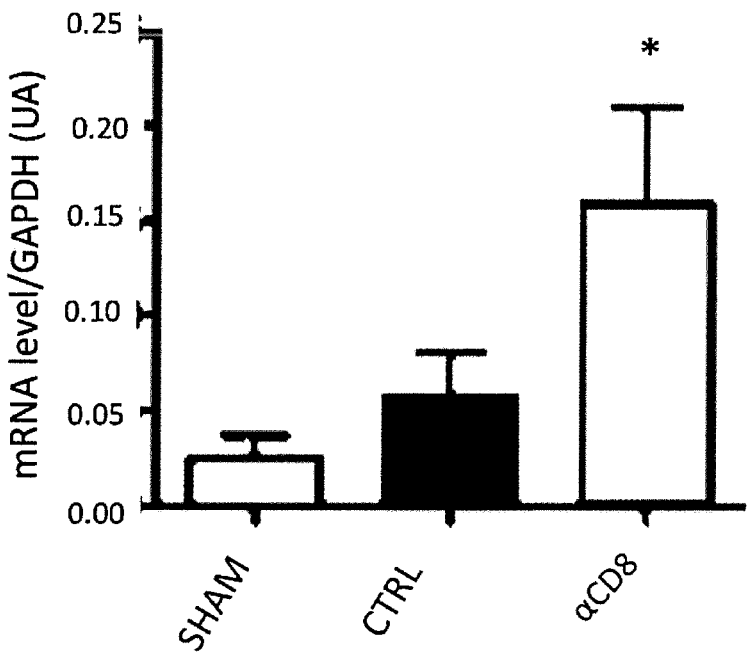

FIG. 7: Metalloprotease Activity at Day 7 after MI, Analysis (A) and representative pictures (B) of zymography showing the catalytic activity of MMP-9 and -2 obtained from myocardial proteins, *: $P<0.05$ (n=4-6/group).

FIG. 8: Gene expression of cytokines (A to E) in the ischemic myocardium at day 7 after acute MI by qPCR. $P<0.05$*(n=4-6/group).

Figure 9:
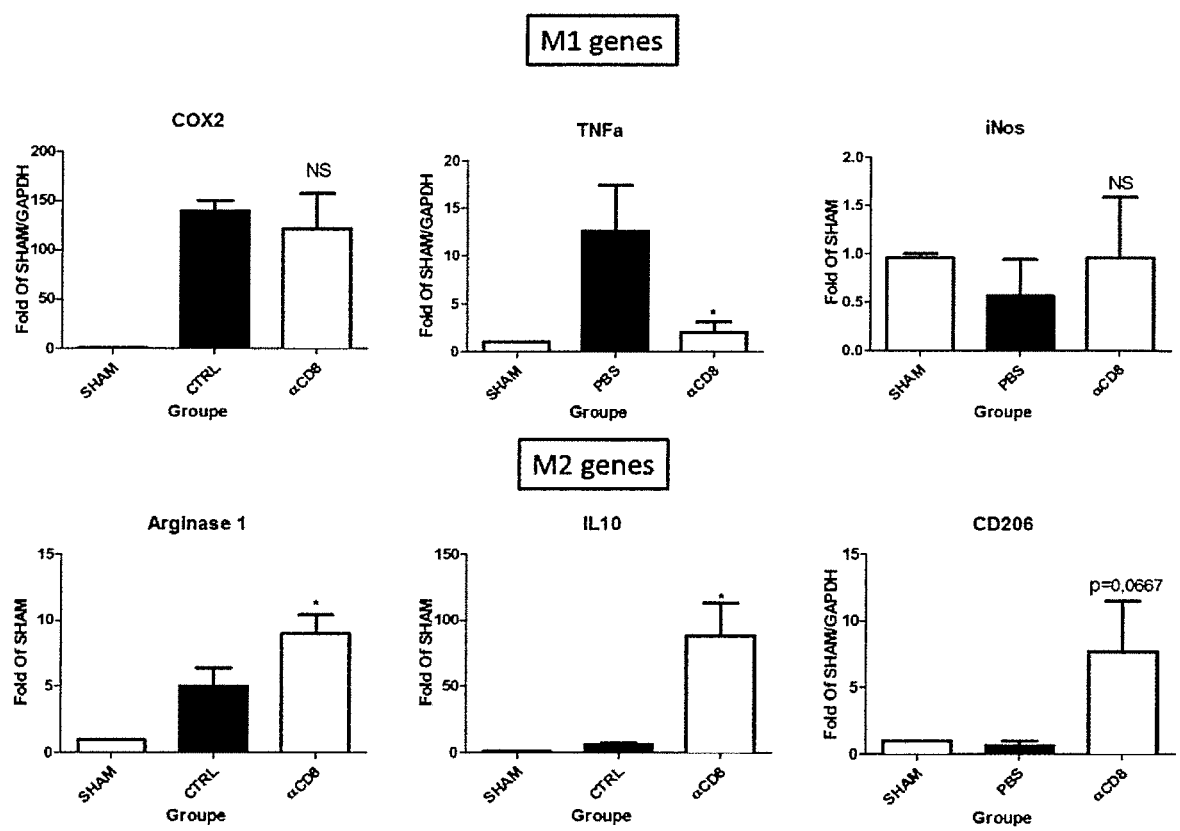

FIG. 9: Gene expression of macrophages from ischemic heart analyzed by qPCR. M1 markers: COX2, iNOS and TNF-a and M2 markers: Arginase-1, IL-10 and CD206 (n=4-6/group).

FIG. 10: Effects of CD8+ T cell depletion on cardiac function. Myocardial infarction was induced in 10-week old C57B16 male mice by left coronary ligature. One hour later, one control group of mice received IgG isotype intraperitoneally (100 μg/mouse n=8) and one group received anti-CD8 depleting antibody IP (100 μg/mouse, n=8). Animals received one additional injection of antibody at day 14.

Figure 11:
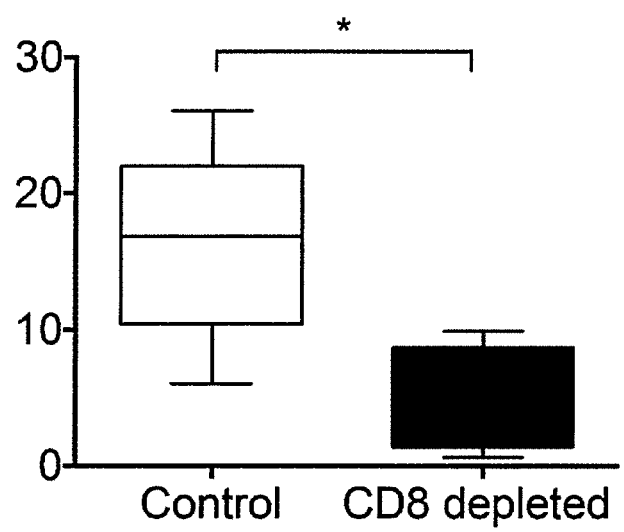

FIG. 11: Long term effects of CD8 T cell depletion on infarct size. Myocardial infarction was induced in 10-week old C57B16 male mice by left coronary ligature. One hour later, one control group received IgG isotype intraperitoneally (100 μg/mouse) and one group received anti-CD8 depleting antibody IP (100 μg/mouse) every 14 days. Animals were sacrificed at day 56 (N=5/group).

EXAMPLE

Material and Method:

Myocardial Infarction

All mice were on a C57BL/6J background. C57BL/6 (Janvier). Myocardial infarction was induced by left coronary ligation (Zouggari et al, Nat Med 2013). Mice were anesthetized using ketamine (100 mg per kg body weight) and xylazine (10 mg per kg body weight) via intraperitoneal injection (i.p.) and then intubated and ventilated with air using a small-animal respirator. The chest wall was shaved and a thoracotomy was performed in the fourth left intercostal space. The left ventricle was visualized, the pericardial sac was then removed, and the left anterior descending artery was permanently ligated using a 7/0 monofilament suture (Peters surgical, France) at the site of its emergence from under the left atrium. Significant color changes at the ischemic area were considered indicative of successful coronary occlusion. The thoracotomy was closed with 6/0 monofilament sutures. The same procedure was performed for sham-operated control mice except that the ligature was left untied. The endotracheal tube was removed once spontaneous respiration resumed, and mice were placed on a warm pad maintained at 37° C. until they were completely awake. One hour after myocardial infarction induction, mice were treated i.p. with a previously validated mouse monoclonal anti-CD8 antibody (200 μg per mouse), with an isotype control. Experiments were conducted according to the French veterinary guidelines and those formulated by the European Community for experimental animal use and were approved by the Institut National de la Santé et de la Recherche Médicale.

Histopathological Analysis

Cardiac healing after myocardial infarction was assessed at day 21. Hearts were excised, rinsed in PBS and frozen in liquid nitrogen. Hearts were cut by a cryostat (CM 3050S, Leica) into 7-μm-thick sections. Masson's Trichrome and Sirius red stainings were performed for infarct size and myocardial fibrosis evaluation. Infarct size (in %) was calculated as total infarct circumference divided by total LV circumference. CD8 T cell immunostaining in human biopsy was performed according to an indirect immunoperoxidase method using a mouse biotin conjugated anti-CD8 antibody (Clone C8/144B, Dako) at a dilution of 1:50.

Cells

Mice were killed at 12 h and on days 1, 3, 5, 7 and 14 after myocardial infarction. Peripheral blood was drawn via inferior vena cava puncture with heparin solution. Whole blood was lysed after immunofluorescence staining using the BD FACS lysing solution (BD Biosciences), and total blood leukocyte numbers were determined using trypan blue. Bone marrow cells were drawn from femur and tibia and filtered through a 40-μm nylon mesh (BD Biosciences). Spleens were collected, minced with fine scissors and filtered through a 40-μm nylon mesh (BD Biosciences). For both splenocytes and bone marrow-derived cells, the cell suspension was centrifuged at 400 g for 10 min at 4° C. Red blood cells were lysed using red blood cell lysing buffer (Sigma-Aldrich) and splenocytes and bone marrow cells were washed with PBS supplemented with 3% (vol/vol) FBS. Hearts were collected, minced with fine scissors and placed into a cocktail of collagenase I (450 U ml$^{-1}$), collagenase XI (125 U ml$^{-1}$), DNase I (60 U ml$^{-1}$), and hyaluronidase (60 U ml$^{-1}$) (Sigma-Aldrich) and shaken at 37° C. for 1 h. Cells were then triturated through a nylon mesh (40 μm) and centrifuged (10 min, 400 g, 4° C.). Mononuclear cells were purified by density centrifugation using Ficoll (Histopaque-1083, Sigma-Aldrich) (25 min, 400 g, room temperature). The resulting cell suspensions were washed using PBS, and total leukocyte numbers were determined.

Flow Cytometry

The following antibodies were used: FITC-conjugated anti-CD11b (M1/70, BD Pharmingen), phycoerythrin (PE)-conjugated anti-Ly6G (1A8, BD Pharmingen), PE-conjugated anti-NK-1.1 (PK 136, BD Pharmingen), allophycocyanin (APC)-conjugated anti-Ly-6B.2 (clone 7/4, AbD Serotec), APC-conjugated anti-CD3e (17A2, eBioscience), FITC-conjugated anti-CD4 (RM 4-5, eBioscience), PercP-conjugated anti-CD8a (53-6.7, BD Pharmingen), PE-conjugated anti-CD45R/B220 (RA3-6B2, eBioscience), APC-conjugated anti-IgM (11/41, eBioscience), PE-Cy7-conjugated anti-CD11c (N418, eBioscience), APC-conjugated anti-CD19 (1D3, BD Pharmingen), APC-conjugated anti-CD45.1 (A20, BD Pharmingen). All antibodies were used at a dilution of 1:100 except for APC-conjugated anti-Ly-6B.2, which was used at 1:20. Monocytes were identified as CD11b$^{hi}$Ly6G$^-$7/4$^{hi/lo}$. Neutrophils were identified as CD11b$^+$Ly6G$^{hi}$7/4$^{hi}$. Macrophages and dendritic cells were identified as CD11c$^{hi}$. Natural killer cells were identified as CD11b$^+$Ly6G$^-$7/4$^-$NK1.1$^+$. Cells were analyzed using a flow cytometer (LSR II, BD Biosciences).

Quantitative Real-Time PCR

Quantitative real-time PCR was performed on a Step-One Plus (Applied Biosystems). GAPDH was used to normalize gene expression. The following primer sequences were used:

| Gene | Sequence | T° of Annealing |
|---|---|---|
| GAPDH | 5'-CGTCCCGTAGACAAAATGGTGAA-3'<br>5'-GCCGTGAGTGGAGTCATACTGGAACA-3' | 61.9° C. |
| IL10 | 5'-AAGTGATGCCCCAGGCA-3'<br>5'-TCTCACCCAGGGAATTCAAA-3' | 61° C. |
| IL-1β | 5'-GAAGAGCCCATCCTCTGTGA-3'<br>5'-GGGTGTGCCGTCTTTCATTA-3' | 59.4° C. |
| IL-6 | 5'-AAAGACAAAGCCAGAGTCCTTCAGAGAGAT-3'<br>5'-GGTCTTGGTCCTTAGCCACTCCTTCTGT-3' | 58.6° C. |
| Granzyme B | 5'-GTGCGGGGGACCCAAAGACCAAAC-3'<br>5'-GCACGTGGAGGTGAACCATCCTTATAT-3' | 62.2° C. |

-continued

| Gene | Sequence | T° of Annealing |
|---|---|---|
| Perforin | 5'-GCAGCTGAGAAGACCTATCAGGACCAGTA-3'<br>5'-TGCGTGCCATAGGAGGAGATGAG-3' | 62.3° C. |
| TNFα | 5'-GATGGGGGCTTCCAGAACT-3'<br>5'-CGTGGGCTACAGGCTTGTCAC-3' | 62.6° C. |
| MMP2 | 5'-CCGAGACCCGCTATGTCCACTGT-3'<br>5'-CCGGTCATCATCATCGTAGTTGGTTGT-3' | 63.8° C. |
| MMP9 | 5'-GCGTCATTCGCGTGGATAAGGAGT-3'<br>5'-GTAGCCCACGTCGTCCACCTGGTT-3' | 62.5° C. |
| TIMP1 | 5'-CCCCCTTTGCATCTCTGGCATCT-3'<br>5'-GCGGTTCTGGGACTTGTGGGCATA-3' | 63.6° C. |
| Arginase-1 | 5'-AGGCCCTGCAGCACTGAGGAA-3'<br>5'-GCCAGGTCCCCGTGGTCTCTCA-3' | 61.1° C. |
| CD206 | 5'-CTATAGGTGGAGAGCTGGCGA-3'<br>5'-TCGCCAGCTCTCCACCTATAG-3' | 57.4° C. |
| iNOS | 5'-TTGGGCCTGGTACGGGCATTG-3'<br>5'-CAAGCTCATGCGGCCTCCTTT-3' | 63.2° C. |
| COX2 | 5'-CCTGCTGCCCGACACCTTCA-3'<br>5'-AGCAACCCGGCCAGCAATCT-3' | 61.1° C. |
| TGFβ1 | 5'-CGGAGAGCCCTGGATACCAACTA-3'<br>5'-GCCGCACACAGCAGTTCTTCTCT-3' | 58.8° C. |

Statistical Analysis

All data are expressed as mean±SE. Comparisons of 2 different groups were analyzed by Mann-Whitney U test. ANOVA test with Bonferroni's post-test analysis was used for more than 2 groups. Statistical analyses were performed with Prism 5 software (GraphPad). P values<0.05 was considered statistically significant.

Results:

Efficacy of Anti-CD8 Depleting Antibody

Intravenous anti-CD8 antibody administration allowed a depletion of more than 95% of CD8+ T cells in the blood, spleen and myocardium (FIG. 1A). The depletion is maintained over the time (FIG. 1B). In the ischemic myocardium, CD8 T depletion is associated with a significant reduction of perforin and granzyme B (mRNA by qPCR), both enzymes produced by cytotoxic CD8+ T cells (FIG. 2).

Effects of CD8 T Cell Depletion on Leukocyte Subset Infiltration

We have recently reported that during acute MI, B cells control monocyte recruitment within the myocardium through Ccl-7 production. In line with these results, we evaluated the effect of CD8 T cell depletion on leukocyte (monocytes, macrophages and neutrophils) recruitment within the ischemic left ventricle using cytometry flow. We didn't observe any difference between the control group and the CD8 T depleted group at Day 1, D3, D6 and D11 following coronary artery ligation (FIG. 3).

CD8 Depletion and Infarct Size

Twenty-one days after MI, animals were sacrificed and we quantified the infarcted area using a Trichrome's Masson staining. In comparison with the control group, we observed a 60% decrease of the infarct size in the CD8-depleted group (P<0.001, FIG. 4). After Sirius red staining, we also found a significant reduction of myocardial fibrosis in the CD8-depleted group (FIG. 5).

Metalloprotease Activity in Ischemic Myocardium

Metalloproteases play a major role in the post-ischemic ventricular remodeling. Interestingly, we found a decrease of MMP-2 and -9 gene expression in the ischemic myocardium of CD8-depleted mice compared to the control group. In addition, Timp-1 mRNA, an inhibitor of metalloproteinases, is increased in the ischemic heart of CD8 depleted mouse (FIG. 6). Using zymography with protein extracts from ischemic myocardium, we confirmed the significant decrease in myocardial catalytic activity of MMP-2 and MMP-9 after anti-CD8 treatment (FIG. 7).

Inflammatory Response in the Ischemic Myocardium

Anti-CD8 treatment significantly altered the cytokine expression profile in the ischemic myocardium. We didn't find any difference between groups regarding mRNA of genes encoding pro-inflammatory cytokines such as Il-1 beta, Il-6 and TNF-alpha. However, we found a significant increase of Il-10 and TGF-beta1 mRNA after CD8 T cell depletion (FIG. 8A to 8E).

Finally, 7 days after myocardial infarction, we isolated heart tissue macrophages using flow cytometry and analyzed their gene expression profile by qPCR. CD8 T cell depletion induced a deviation of macrophage polarization toward a M2 phenotype with a significant increase in Arginase-1, Il-10 mRNA and a trend to an increase of CD206 (Mannose Receptor) mRNA. Expression of M1 genes such as iNos and Cox-2 were not different between both groups. Finally, there was a significant decrease in expression of TNF-alpha mRNA in macrophages from CD8-depleted mice (FIG. 9).

CD8 T Infiltration in Human Ischemic Heart

Finally, we analyzed CD8 T cell infiltration in human myocardial biopsy of patients suffering from myocardial infarction by immunohistochemistry. We observed an infiltration at the early stage of the ischemic event (1 day) in the peri-vascular and peri-infarct area. (FIG. 10 A). CD8 T cell infiltration was more pronounced in the later stage of the MI (7 days) (FIG. 10 B).

Effects of CD8+ T Cell Depletion on Cardiac Function

Myocardial infarction was induced in 10-week old C57B16 male mice by left coronary ligature. One hour later, one control group of mice received IgG isotype intraperitoneally (100 µg/mouse n=8) and one group received anti-CD8 depleting antibody IP (100 µg/mouse, n=8). Animals received one additional injection of antibody at day 14.

CD8 depletion in the blood was confirmed by flow cytometry at day 9 and day 28. Left ventricular function was evaluated blindly by echocardiography at day 9 and day 28. In addition at day 28, cardiac function was evaluated invasively using left ventricular catheterization. As depicted below, we found that CD8 T cell depletion was protective as left ventricular systolic function was significantly higher in CD8-depleted animals at both day 9 and day 28 following MI in comparison with isotype-treated animals (FIG. 1A). CD8 depletion limited deleterious left ventricular remodeling as left ventricular telediastolic diameter was significantly lower in CD8-depleted animals (FIG. 1B). At sacrifice, using a Millar ventricular catheter, we measured several parameters that reflect cardiac contractility (dP/dt max) and relaxation (dP/dtmin). As showed below, CD8 T cell depletion improved both hemodynamic parameters after myocardial infarction.

Long Term Effects of CD8 T Cell Depletion on Infarct Size

Myocardial infarction was induced in 10-week old C57B16 male mice by left coronary ligature. One hour later, one control group received IgG isotype intraperitoneally (100 µg/mouse) and one group received anti-CD8 depleting antibody IP (100 µg/mouse) every 14 days. Animals were sacrificed at day 56 (N=5/group). Infarct size was quantified after Masson's Trichrome staining. As depicted below, infarct size was significantly smaller in CD8 depleted animals at day 56 suggesting that protective effects of CD8 depletion were sustained over the time.

CONCLUSION

For the first time, the inventors have shown that the CD8+ T cell depletion by injection of an anti-CD8 monoclonal antibody in a mouse model of myocardial infarction induced a significant reduction in the size of necrosis, reduced deleterious remodeling such as evidenced by the decrease in fibrosis peri-necrotic and causes a deviation of the local immune response to an anti-inflammatory profile. These results are encouraging and could provide a new therapeutic approach to limit deleterious left ventricular remodeling in post-myocardial infarction.

Throughout this application, various references describe the state of the art to which this invention pertains. The disclosures of these references are hereby incorporated by reference into the present disclosure.

REFERENCES

1. Puymirat, E., et al., *Association of changes in clinical characteristics and management with improvement in survival among patients with ST-elevation myocardial infarction*. JAMA, 2012. 308(10): p. 998-1006.
2. Frangogiannis, N. G., *Regulation of the inflammatory response in cardiac repair*. Circ Res, 2012. 110(1): p. 159-73.
3. Silvestre, J. S., D. M. Smadja, and B. I. Levy, *Postischemic revascularization: from cellular and molecular mechanisms to clinical applications*. Physiol Rev, 2013. 93(4): p. 1743-802.
4. Romson, J. L., et al., *Reduction of the extent of ischemic myocardial injury by neutrophil depletion in the dog*. Circulation, 1983. 67(5): p. 1016-23.
5. Zouggari, Y., et al., *B lymphocytes trigger monocyte mobilization and impair heart function after acute myocardial infarction*. Nat Med, 2013. 19(10): p. 1273-80.
6. Weirather, J., et al., *Foxp3+CD4+ T cells improve healing after myocardial infarction by modulating monocyte/macrophage differentiation*. Circ Res, 2014. 115(1): p. 55-67.
7. Varda-Bloom, N., et al., *Cytotoxic T lymphocytes are activated following myocardial infarction and can recognize and kill healthy myocytes in vitro*. J Mol Cell Cardiol, 2000. 32(12): p. 2141-9.
8. Bourgeois, C. and B. Stockinger, *CD25+CD4+ regulatory T cells and memory T cells prevent lymphopenia-induced proliferation of naive T cells in transient states of lymphopenia*. J Immunol, 2006. 177(7): p. 4558-66.

The invention claimed is:

1. A method for treating myocardial infarction (MI) or acute myocardial infarction (AMI) in a subject in need thereof comprising the step of administering to said subject within 14 days of the infarction a therapeutically effective amount of an anti-CD8 antibody capable of depleting CD8 T cells.

2. The method of claim 1, wherein the anti-CD8 antibody is a monoclonal antibody.

3. The method of claim 1, wherein the anti-CD8 antibody is a monoclonal antibody conjugated to a cytotoxic agent.

\* \* \* \* \*

```
                        SEQUENCE LISTING

<160> NUMBER OF SEQ ID NOS: 30

<210> SEQ ID NO 1
<211> LENGTH: 23
<212> TYPE: DNA
<213> ORGANISM: Artificial
<220> FEATURE:
<223> OTHER INFORMATION: Synthetic primer sequence 1 for GAPDH

<400> SEQUENCE: 1
cgtcccgtag acaaaatggt gaa                                            23

<210> SEQ ID NO 2
<211> LENGTH: 26
<212> TYPE: DNA
<213> ORGANISM: Artificial
<220> FEATURE:
<223> OTHER INFORMATION: Synthetic primer sequence 2 for GAPDH

<400> SEQUENCE: 2
gccgtgagtg gagtcatact ggaaca                                         26
```

```
<210> SEQ ID NO 3
<211> LENGTH: 17
<212> TYPE: DNA
<213> ORGANISM: Artificial
<220> FEATURE:
<223> OTHER INFORMATION: Synthetic primer sequence 1 for IL10

<400> SEQUENCE: 3
aagtgatgcc ccaggca                                                   17

<210> SEQ ID NO 4
<211> LENGTH: 20
<212> TYPE: DNA
<213> ORGANISM: Artificial
<220> FEATURE:
<223> OTHER INFORMATION: Synthetic primer sequence2 for IL10

<400> SEQUENCE: 4
tctcacccag ggaattcaaa                                                20

<210> SEQ ID NO 5
<211> LENGTH: 20
<212> TYPE: DNA
<213> ORGANISM: Artificial
<220> FEATURE:
<223> OTHER INFORMATION: Synthetic primer sequence 1 for IL-1beta

<400> SEQUENCE: 5
gaagagccca tcctctgtga                                                20

<210> SEQ ID NO 6
<211> LENGTH: 20
<212> TYPE: DNA
<213> ORGANISM: Artificial
<220> FEATURE:
<223> OTHER INFORMATION: Synthetic primer sequence 2 for IL-1beta

<400> SEQUENCE: 6
gggtgtgccg tctttcatta                                                20

<210> SEQ ID NO 7
<211> LENGTH: 30
<212> TYPE: DNA
<213> ORGANISM: Artificial
<220> FEATURE:
<223> OTHER INFORMATION: Synthetic primer sequence 1 for IL-6

<400> SEQUENCE: 7
aaagacaaag ccagagtcct tcagagagat                                     30

<210> SEQ ID NO 8
<211> LENGTH: 28
<212> TYPE: DNA
<213> ORGANISM: Artificial
<220> FEATURE:
<223> OTHER INFORMATION: Synthetic primer sequence 2 for IL-6

<400> SEQUENCE: 8
ggtcttggtc cttagccact ccttctgt                                       28

<210> SEQ ID NO 9
<211> LENGTH: 24
<212> TYPE: DNA
<213> ORGANISM: Artificial
<220> FEATURE:
<223> OTHER INFORMATION: Synthetic primer sequence 1 for Granzyme B
```

```
<400> SEQUENCE: 9
gtgcggggga cccaaagacc aaac                                          24

<210> SEQ ID NO 10
<211> LENGTH: 27
<212> TYPE: DNA
<213> ORGANISM: Artificial
<220> FEATURE:
<223> OTHER INFORMATION: Synthetic primer sequence 2 for Granzyme B

<400> SEQUENCE: 10
gcacgtggag gtgaaccatc cttatat                                       27

<210> SEQ ID NO 11
<211> LENGTH: 29
<212> TYPE: DNA
<213> ORGANISM: Artificial
<220> FEATURE:
<223> OTHER INFORMATION: Synthetic primer sequence 1 for Perforin

<400> SEQUENCE: 11
gcagctgaga agacctatca ggaccagta                                     29

<210> SEQ ID NO 12
<211> LENGTH: 23
<212> TYPE: DNA
<213> ORGANISM: Artificial
<220> FEATURE:
<223> OTHER INFORMATION: Synthetic primer sequence 2  for Perforin

<400> SEQUENCE: 12
tgcgtgccat aggaggagat gag                                           23

<210> SEQ ID NO 13
<211> LENGTH: 20
<212> TYPE: DNA
<213> ORGANISM: Artificial
<220> FEATURE:
<223> OTHER INFORMATION: Synthetic primer sequence 1  for TNF alpha

<400> SEQUENCE: 13 gatgggggc ttccagaact                                                20

<210> SEQ ID NO 14
<211> LENGTH: 21
<212> TYPE: DNA
<213> ORGANISM: Artificial
<220> FEATURE:
<223> OTHER INFORMATION: Synthetic primer sequence 2 for TNF alpha

<400> SEQUENCE: 14
cgtgggctac aggcttgtca c                                             21

<210> SEQ ID NO 15
<211> LENGTH: 23
<212> TYPE: DNA
<213> ORGANISM: Artificial
<220> FEATURE:
<223> OTHER INFORMATION: Synthetic primer sequence 1  for MMP2

<400> SEQUENCE: 15
ccgagacccg ctatgtccac tgt                                           23

<210> SEQ ID NO 16
```

```
<211> LENGTH: 27
<212> TYPE: DNA
<213> ORGANISM: Artificial
<220> FEATURE:
<223> OTHER INFORMATION: Synthetic primer sequence 2 for MMP2

<400> SEQUENCE: 16
ccggtcatca tcatcgtagt tggttgt                                          27

<210> SEQ ID NO 17
<211> LENGTH: 24
<212> TYPE: DNA
<213> ORGANISM: Artificial
<220> FEATURE:
<223> OTHER INFORMATION: Synthetic primer sequence 1 for MMP9

<400> SEQUENCE: 17
gcgtcattcg cgtggataag gagt                                             24

<210> SEQ ID NO 18
<211> LENGTH: 24
<212> TYPE: DNA
<213> ORGANISM: Artificial
<220> FEATURE:
<223> OTHER INFORMATION: Synthetic primer sequence 2 for MMP9

<400> SEQUENCE: 18
gtagcccacg tcgtccacct ggtt                                             24

<210> SEQ ID NO 19
<211> LENGTH: 23
<212> TYPE: DNA
<213> ORGANISM: Artificial
<220> FEATURE:
<223> OTHER INFORMATION: Synthetic primer sequence 1 for TIMP1

<400> SEQUENCE: 19
ccccctttgc atctctggca tct                                              23

<210> SEQ ID NO 20
<211> LENGTH: 24
<212> TYPE: DNA
<213> ORGANISM: Artificial
<220> FEATURE:
<223> OTHER INFORMATION: Synthetic primer sequence 2 for TIMP1

<400> SEQUENCE: 20
gcggttctgg gacttgtggg cata                                             24

<210> SEQ ID NO 21
<211> LENGTH: 21
<212> TYPE: DNA
<213> ORGANISM: Artificial
<220> FEATURE:
<223> OTHER INFORMATION: Synthetic primer sequence 1 for Arginase-1

<400> SEQUENCE: 21
aggccctgca gcactgagga a                                                21

<210> SEQ ID NO 22
<211> LENGTH: 22
<212> TYPE: DNA
<213> ORGANISM: Artificial
<220> FEATURE:
<223> OTHER INFORMATION: Synthetic primer sequence 2 for Arginase-1

<400> SEQUENCE: 22
```
gccaggtccc cgtggtctct ca                                                    22

<210> SEQ ID NO 23
<211> LENGTH: 21
<212> TYPE: DNA
<213> ORGANISM: Artificial
<220> FEATURE:
<223> OTHER INFORMATION: Synthetic primer sequence 1 for CD206

<400> SEQUENCE: 23
ctataggtgg agagctggcg a                                                     21

<210> SEQ ID NO 24
<211> LENGTH: 21
<212> TYPE: DNA
<213> ORGANISM: Artificial
<220> FEATURE:
<223> OTHER INFORMATION: Synthetic primer sequence 2 for CD206

<400> SEQUENCE: 24
tcgccagctc tccacctata g                                                     21

<210> SEQ ID NO 25
<211> LENGTH: 21
<212> TYPE: DNA
<213> ORGANISM: Artificial
<220> FEATURE:
<223> OTHER INFORMATION: Synthetic primer sequence 1 for iNOS

<400> SEQUENCE: 25
ttgggcctgg tacgggcatt g                                                     21

<210> SEQ ID NO 26
<211> LENGTH: 21
<212> TYPE: DNA
<213> ORGANISM: Artificial
<220> FEATURE:
<223> OTHER INFORMATION: Synthetic primer sequence 2 for iNOS

<400> SEQUENCE: 26
caagctcatg cggcctcctt t                                                     21

<210> SEQ ID NO 27
<211> LENGTH: 20
<212> TYPE: DNA
<213> ORGANISM: Artificial
<220> FEATURE:
<223> OTHER INFORMATION: Synthetic primer sequence 1 for COX2

<400> SEQUENCE: 27
cctgctgccc gacaccttca                                                       20

<210> SEQ ID NO 28
<211> LENGTH: 20
<212> TYPE: DNA
<213> ORGANISM: Artificial
<220> FEATURE:
<223> OTHER INFORMATION: Synthetic primer sequence 2 for COX2

<400> SEQUENCE: 28
agcaacccgg ccagcaatct                                                       20

<210> SEQ ID NO 29
<211> LENGTH: 23
<212> TYPE: DNA

```
<213> ORGANISM: Artificial
<220> FEATURE:
<223> OTHER INFORMATION: Synthetic primer sequence 1 for TGFbeta1

<400> SEQUENCE: 29
cggagagccc tggataccaa cta                                              23

<210> SEQ ID NO 30
<211> LENGTH: 23
<212> TYPE: DNA
<213> ORGANISM: Artificial
<220> FEATURE:
<223> OTHER INFORMATION: Synthetic primer sequence 2 for TGFbeta1

<400> SEQUENCE: 30
gccgcacaca gcagttcttc tct                                              23
```